Figure 2:
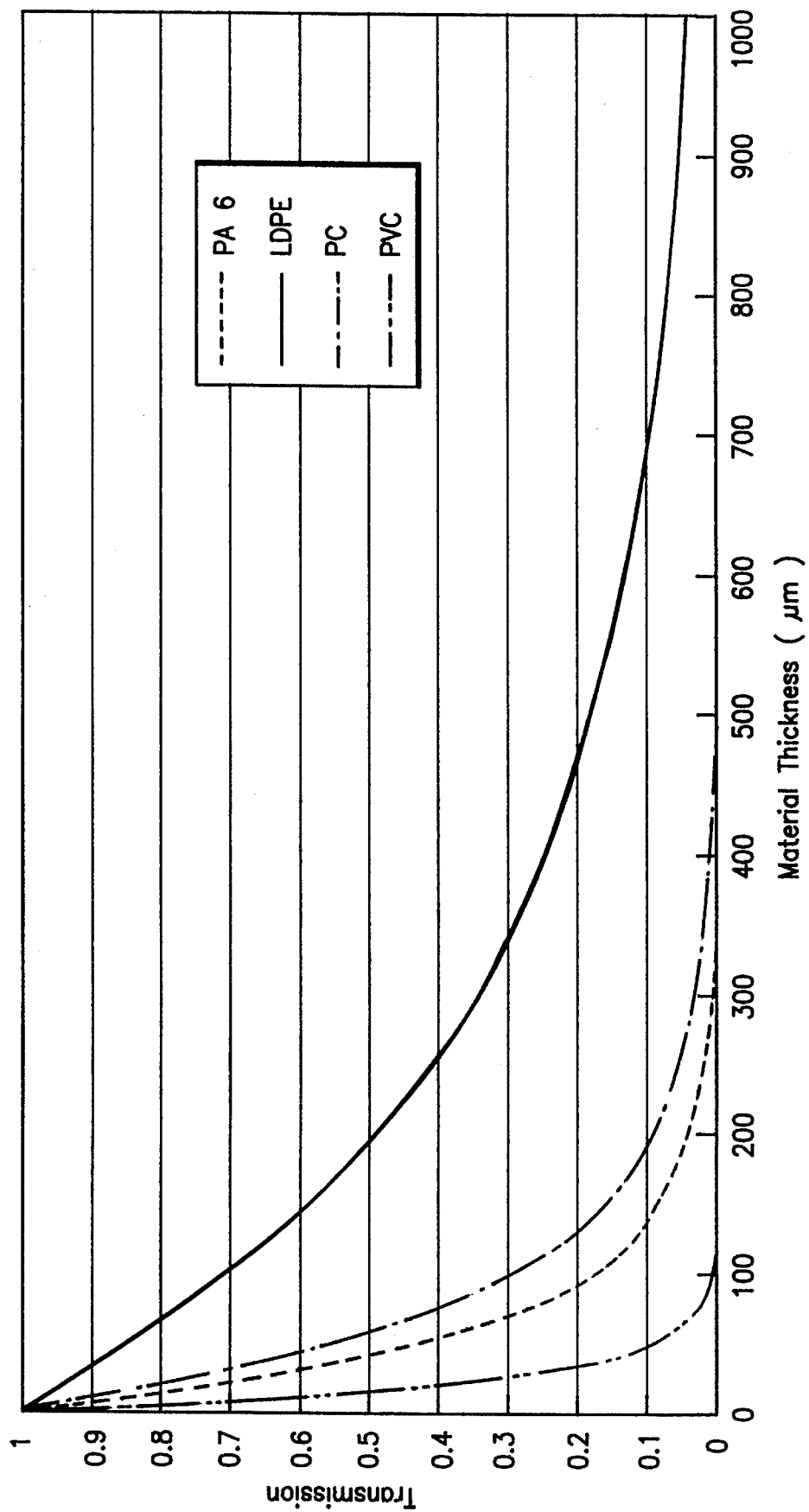

United States Patent [19]
Burmester et al.

[11] Patent Number: 5,489,778
[45] Date of Patent: Feb. 6, 1996

[54] PROCESS AND INSTALLATION FOR THE IDENTIFICATION OF MATERIALS

[75] Inventors: Ingo Burmester; Kurt Engel, both of Hanover, Germany

[73] Assignee: Laser Zentrum Hannover e.V., Hanover, Germany

[21] Appl. No.: 154,065

[22] Filed: Nov. 18, 1993

[30] Foreign Application Priority Data

Nov. 21, 1992 [DE] Germany ......................... 42 39 479.1

[51] Int. Cl.$^6$ .......................... G01N 21/71; G01N 25/18
[52] U.S. Cl. ................. 250/341.6; 250/330; 250/339.08; 250/341.1
[58] Field of Search ............................. 250/341, 339.06, 250/339.07, 339.08, 330, 341.8, 341.6, 341.1

[56] References Cited

U.S. PATENT DOCUMENTS

| | | | |
|---|---|---|---|
| 4,928,254 | 5/1990 | Knudsen et al. | 364/556 |
| 5,075,552 | 12/1991 | McClelland et al. | 250/341 |
| 5,118,945 | 6/1992 | Winschuh et al. | 250/341 |

OTHER PUBLICATIONS

Otto Renius, "Laser Illumination for Infrared Nondestructive Testing." *Materials Evaluation* (May 1973) pp. 80–84.

*Primary Examiner*—Constantine Hannaher
*Attorney, Agent, or Firm*—Shlesinger Arkwright & Garvey

[57] ABSTRACT

Materials are exposed to laser energy, and after the material is heated, the thermal radiation of the material is measured. Following this, a material-specific evaluation takes place, based on optical and thermal material properties. At least one area on the surface of the material to be identified is subject to a short, point-shaped exposure of laser radiation. The material-specific thermal impulse response for the radiated surface area of the material is both locally and temporally measured, and evaluated as regarding the kind of material.

24 Claims, 14 Drawing Sheets

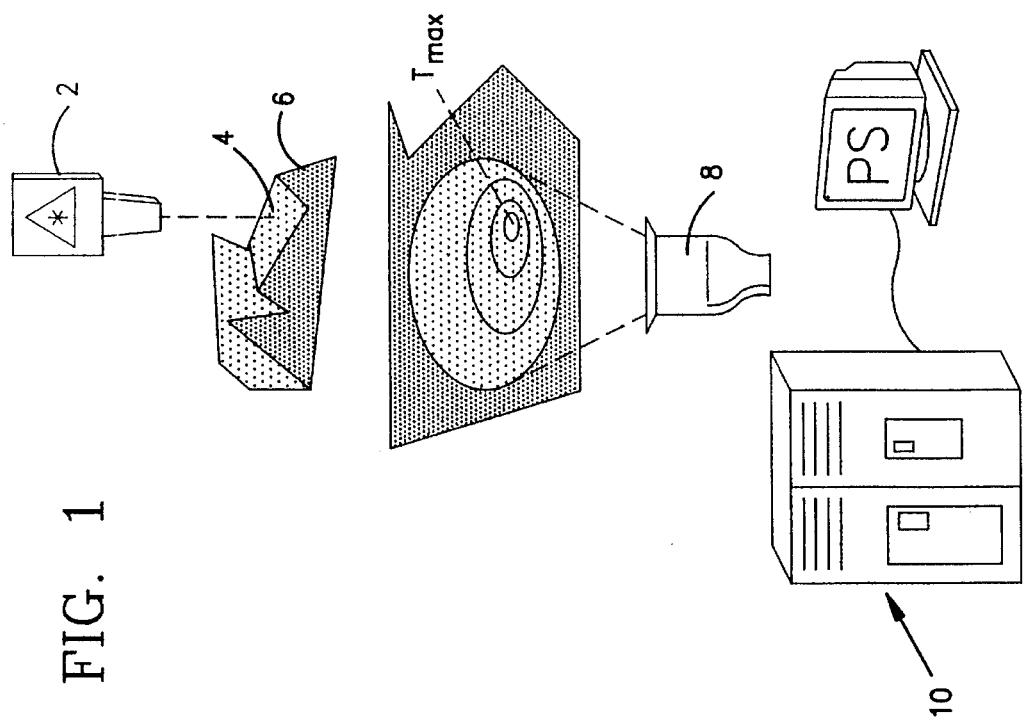
FIG. 1
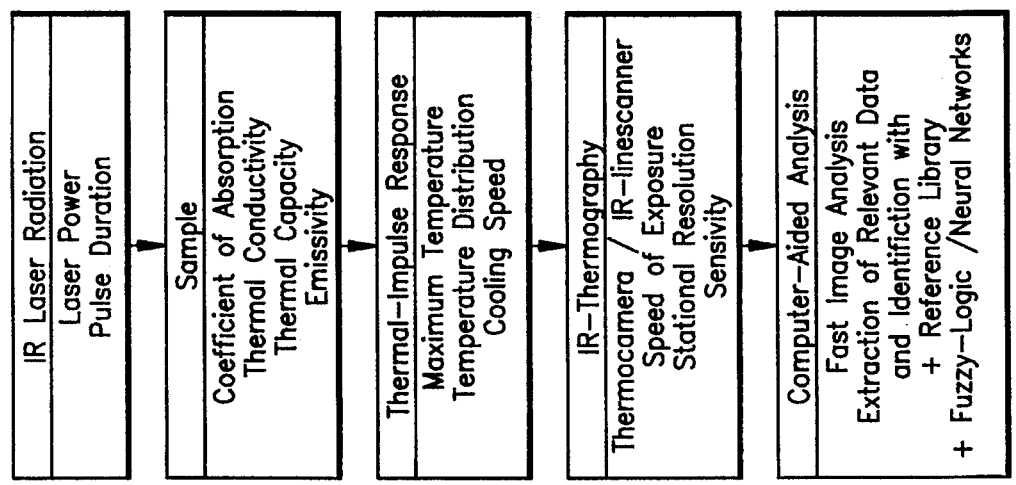

FIG. 9

| Plastics | Symbol | Temperature Conductivity (cm²/s) | Thermal Conductivity (W/mk) | Thermal Capacity (J/gk) | Density (g/cm³) | Melting Point (°C) |
|---|---|---|---|---|---|---|
| Polypropylene | PP | 1.5 | 0.22 | 1.7 | 0.86 | 160–168 |
| Polyamide 6 | PA 6 | 1.48–1.52 | 0.29 | 1.7 | 1.12–1.15 | 180–260 |
| Polyamide 66 | PA 66 | 1.26–1.3 | 0.2–0.3 | 1.7 | 1.13–1.16 | 180–260 |
| Polyethylene HD | HDPE | 2.3–2.36 | 0.4 | 1.8 | 0.94–0.965 | 130–137 |
| Polyethylene LD | LDPE | 1.64–1.67 | 0.32 | 2.1 | 0.914–0.928 | 108–116 |
| Acrylonitrile butadiene styrene CP | ABS | 1.13–1.17 | 0.18 | 1.5 | 1.02–1.06 | 180–241 |
| Polycarbonate | PC | 1.46 | 0.21 | 1.2 | 1.2 | 140–150 |
| Polyvinyl chloride | PVC | 1.17–1.53 | 0.16 | 0.9 | 1.16–1.52 | 80–90 |
| Polyphenylene ether | PPE (PPO) | 1.58 | 0.23 | 1.4 | 1.04 | – |
| Polymethylmethacrylate | PMMA | 1.0–1.03 | 0.18 | 1.5 | 1.17–1.2 | 90–105 |
| Styrene acrylonitrile CP | SAN | 1.28 | 0.18 | 1.3 | 1.08 | 200–265 |
| Polyethylene terephtalate | PET | 1.31 | 0.27 | 1.5 | 1.37 | – |
| Polystyrene | PS | 1.17–1.18 | 0.16 | 1.3 | 1.04–1.05 | 88–100 |
| Polytetrafluoro ethylene | PTFE | 1.07–1.05 | 0.23 | 1.0 | 2.15–2.2 | – |

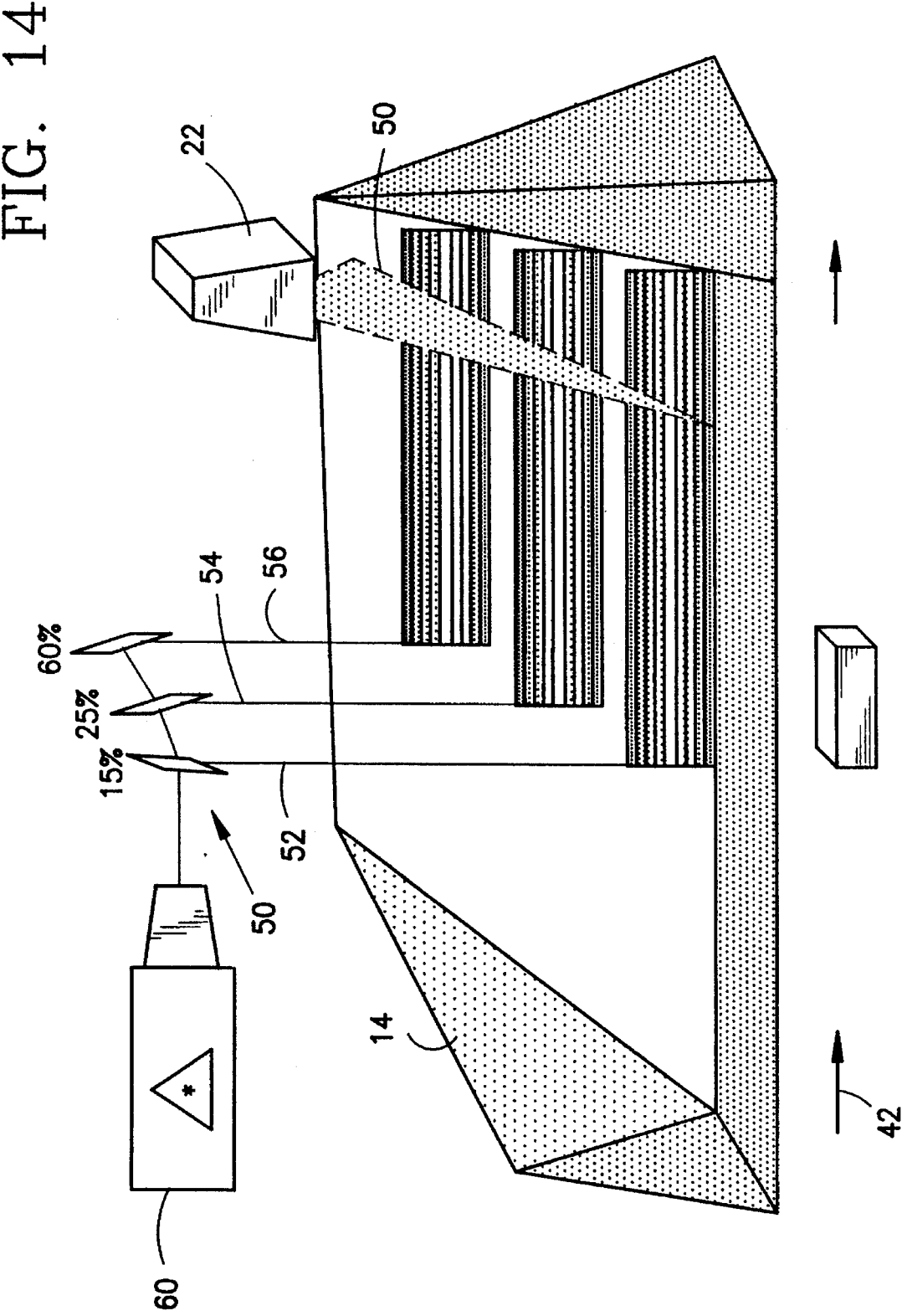

PROCESS AND INSTALLATION FOR THE IDENTIFICATION OF MATERIALS

The invention consists of process and an installation for the identification of materials in which the materials are exposed to laser energy, and after the material is heated, the thermal radiation of the materials is measured, after which the material are evaluated according to their optical and thermal properties.

In connection with material recycling, the question arises as to how different materials which cannot be recycled together can be separated as automatically as possible. For the recycling of materials, it is of decisive importance that the materials are not mixed, because material quality decreases drastically the higher the mixture of the materials.

At present, the identification and separation of different plastic materials is often carried out by manual sorting methods. The uneconomicalness and the low efficiency of manual sorting methods, reduce their use to the sorting of larger, whole plastic parts, as in the recycling of car parts. This method is not suitable for the sorting of smaller plastic parts which are typical of rubbish and packaging waste, compare D. Braun, Deutsches Kunststoffinstitut (German institute of synthetics) "Einfache Methoden zur Kunststofferkennung", speech by DVM Tag 1992 "Bauteil 1992", Berlin. To recycle smaller plastic parts, it is necessary to link automatic plastic identification with the following automatic separation, compare "Sortenreines Recycling setzt eindeutige Produktbezeichnung voraus", Österreich. Kunstst. paper 1990, edition 21 (5/b), S. 113–115.

Today there are two automatic separation process which, to a limited extent, can only be used for certain plastics.

One separation process which is currently used on a larger technical scale is the separation of plastics according to their specific density. For this process, the plastics are subdivided into light fractions and heavy fractions. (G. Hörber, G. Ropertz, P. Kaniut "Das AKW-Kunststoffaufbereitungssystem-eine moderne und wirtschaftliche Alternative für die Wiederverwertung von Alt-Kunststoffen, in der Aufbereitungs-Technik" (1989), Asg. 30(8), S. 300–306; A. Ansems, "Kunststoffe aus Abfällen. Trennung an der Quelle bestimmt die Wiederverwendungsmöglichkeiten", in paper Kunstst. Rubber (1988), Aus. 41(12), S. 62–69; A. Funke, J. Noack, "Homogenisieren von Sekundärpolyolefinen", in paper Plaste Kautschuk (1987), Aus. 34(2), S. 72–73. The polyolefines, belong to the light fraction, whereas polyethylene or polypropylene need further separation, because they cannot be recycled as a mixture. The heavy fraction consists of all the other plastic materials, and also needs further separation before recycling. The further separation of these fractions by means of their specific density leads to high material impurities. This method is technically carried out by a hydrocyclone and a float and sink gutter in combination with water, which separates the plastics.

Another technical process of flotation is based on the fact that air bubbles settle on the hydrophobic surface of plastics, which cause these materials to float in water. By adding a specific amount of reagents, it is possible to prevent the air bubbles from adhering to certain plastics. (E. Kroker, R&D project, "Pilotvorhaben zum Trennen und Aufbereiten von Kunststoffen aus Haushalts- und Gewerbeabfällen", information of the "Amtlichen Material Prüfanstalt", Hannover, 1989). The disadvantages of this method are, on the one hand, the limited separation in only two synthetic fractions per application, and on the other hand, the possible influence on the plastics caused by the contact with the separation reagent. Moreover, as the separation depends on the surface of the material, only clean and uncoated plastics can be separated, which means a further drastical restriction of this method.

Further methods for the identification of plastics have been suggested which, however, are far from being a solution to the sorting problem, and the technical application of those methods can almost be excluded.

One process for the identification of plastics is based on identifying the plastics by a fluorescent color which has to be added when the plastics are produced. (K. Luttermann, A. Becker, Bayer AG, "Kennzeichnung von Kunststoffen mit Floureszenzfarbstoffen", speech by DVM Tag 1992 "Bauteil 1992", Berlin). When the plastics are exposed to light, their fluorescence makes the reliable identification of the plastics possible. This method requires that all the manufacturers of plastics reach an agreement about standardized, material specific additions of fluorescent colors when the plastics are produced. Therefore, it can be problematic to carry through the necessary and general introduction and standardization of the addition of flourescent colors. A similar method is based on the X-ray fluorescent analysis in which, depending on the plastic, doping agents or aggregates which make the identification possible have to be added during the production. (K. H. Folkerts, Vortrag im 38 A. Dechema-Kolloquium, 30.1.1992, Frankfurt/Main). Another method is to identify the plastics by means of an AOTF-reflection spectrometer. (N. Eisenreich, speech by 384. Dechema-Kolloquium, 30.1.1992, Frankfurt/Main; N. Eisenreich, M. Krause, H. Kutt, Th. Messer, "Schnelle Erkennung von Kunststoffen mit AOTF-Reflexionsspektrometer", VDI informatione Nr. 934, 1991, S. 447–459) in which the NIR-reflection spectrum is used for the identification of different plastics. The reflection spectrum of the near infrared frequency (1000 to 2500 nm) contains enough information to identify the plastics. The quick evaluation of the very complicated spectrums in, which in addition change extremely, depending on the additives, colors and the different other additions. Furthermore, it is problematic to identify dirty or filled plastics. This method is technically very demanding.

It was also suggested to identify the plastics by examining the thermal decomposition products of the plastics by means of mass spectrometry. (H. Müller von der Haagen, speech by 384. Dechema-Kolloquium, 30.1.1992, Frankfurt/Main). When this method is used, the plastics can only be indirectly identified by their pyrolysis products. Problems can occur when the gaseous products are transferred into the high-vacuum of the mass spectrometer. It should also be considered that the combination of thermal decomposition, MS-analysis, and the following evaluation is very time-consuming. Moreover, some pyrolysis products of the different plastics are partially identical, which also makes separation more difficult.

Investigations on using separating liquids for sorting plastic mixtures according to their specific density have also been carried out. (U. Leuning, "Kunststoffrecycling in Italien, Ziel der Regierung in eine Rücklaufquote bei Kunststoffverpackungen von 40%", paper Umwelt, edition 20(4), 1990, S. 164–166). Again, it was impossible to reliably distinguish between the different plastics, because their specific densities were too similar. In the USA, an electromagnetic separation method was developed (R. T. Gottesmann, speech by IUPAC International Symposium Recycling of Polymeres, Marbella, Spain 18.–20. Sep., 1991) which only makes the separation of PVC from polyolefines possible, and thus it cannot be expected that this method will serve as a solution to the complex separation problem of mixed plastics.

In summary, it can be said that the known methods are not a technical solution to recycling of mixed plastics.

The task of the present invention is to offer a process and an installation for the quick and reliable identification of different materials.

The invention makes the use of the fact that specific thermal and optical properties of different materials can be analyzed. To do so, laser energy is projected onto the surface of the material, and the local and temporal heat radiation is measured and evaluated by means of pyrometic temperature measurement. In accordance with the thermal and optical properties of the material, such as the absorption coefficient, the thermal conductivity, the thermal capacity and the emission rate, the temporal (rate of cooling) as well as the local (distribution of heat) differences can be detected through the thermal impulse response of the different materials. The thermal impulse response is characterized by the maximum temperature directly after the laser exposure, the heat distribution and the cooling period.

A thermocamera, or more simply a pyrometer which is sufficient for punctual temperature measurement is suitable for stationary material analysis. If moving materials are to be measured, the thermal impulse response can be measured by an IR-linescanner, because the motion of the material makes IR-measurement of the motion axis automatically possible. The recording of the analysis signal which can be a sorting signal is carried out by a computer-aided evaluation system which evaluates the thermal impulse response received by means of pyrometry. It is possible to use reference libraries as well as fuzzy logic or neuronal networks to evaluate the typical material properties the thermal impulse response. By means of the computer-aided evaluation, it is possible to evaluate up to 50 analysis steps per second, and thus, the reliability of identification increases by multiple measurement of the material.

The use of a $CO_2$ laser, which is characterized by a laser wavelength of 10.6 µm, offers the following advantages due to the wavelength in the IR-range: Frequently, pigment dyestuffs are added to plastics which influence the radiation absorption in the proximity of the visible wavelength range and thus disturb the thermal impulse response. In a wavelength range, of about 10.6 µm, the dyes have no absorbing effect, so to that the thermal impulse response is not disturbed. The use of laser beams within the middle IR-range reduces the influence of the surface angle of the examined material. Especially if laser beams within the mid IR-range are used for the identification of plastics, it comes due to the comparatively high absorption surface absorption instead of volume absorption, and thus it is also possible to examine thin plastics.

In the following section, the invention is explained in more detail, with the help of the included pictures, which also gives examples of the construction.

Figure 3:
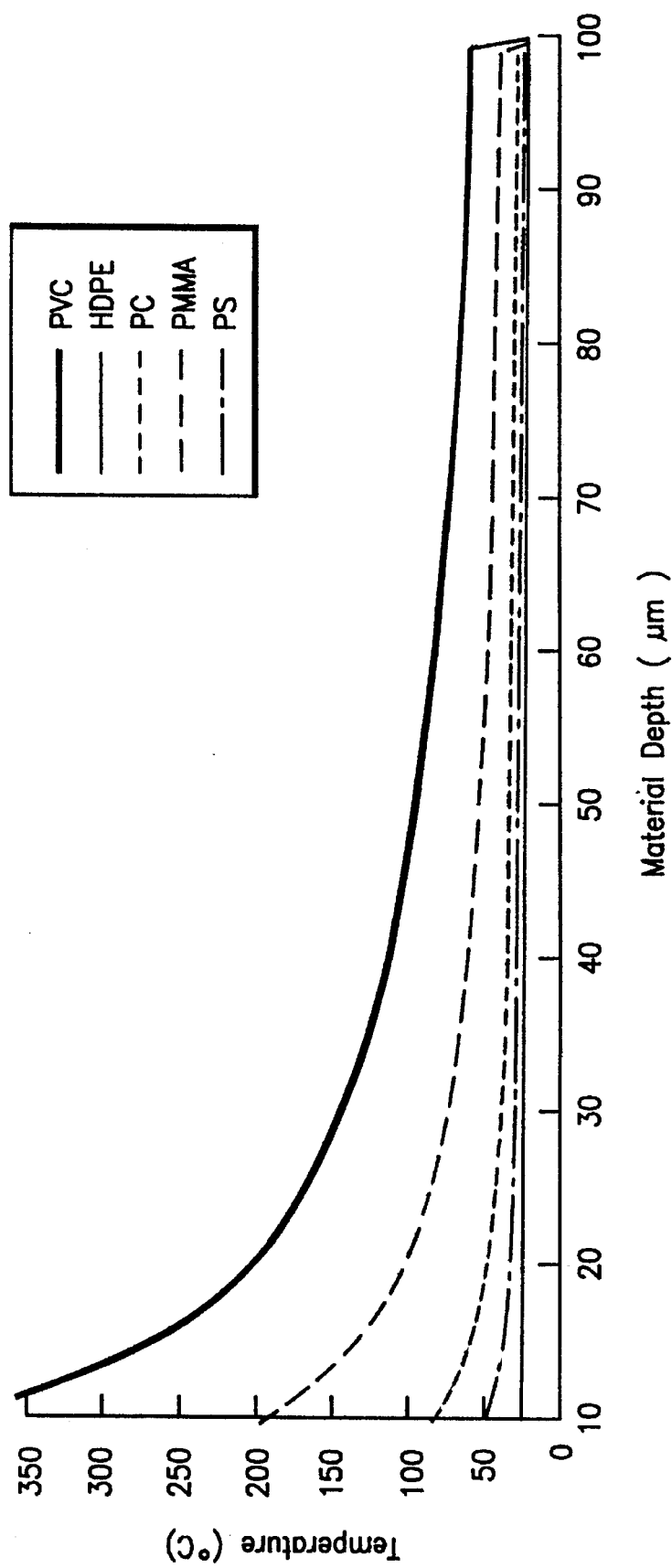
Figure 4:
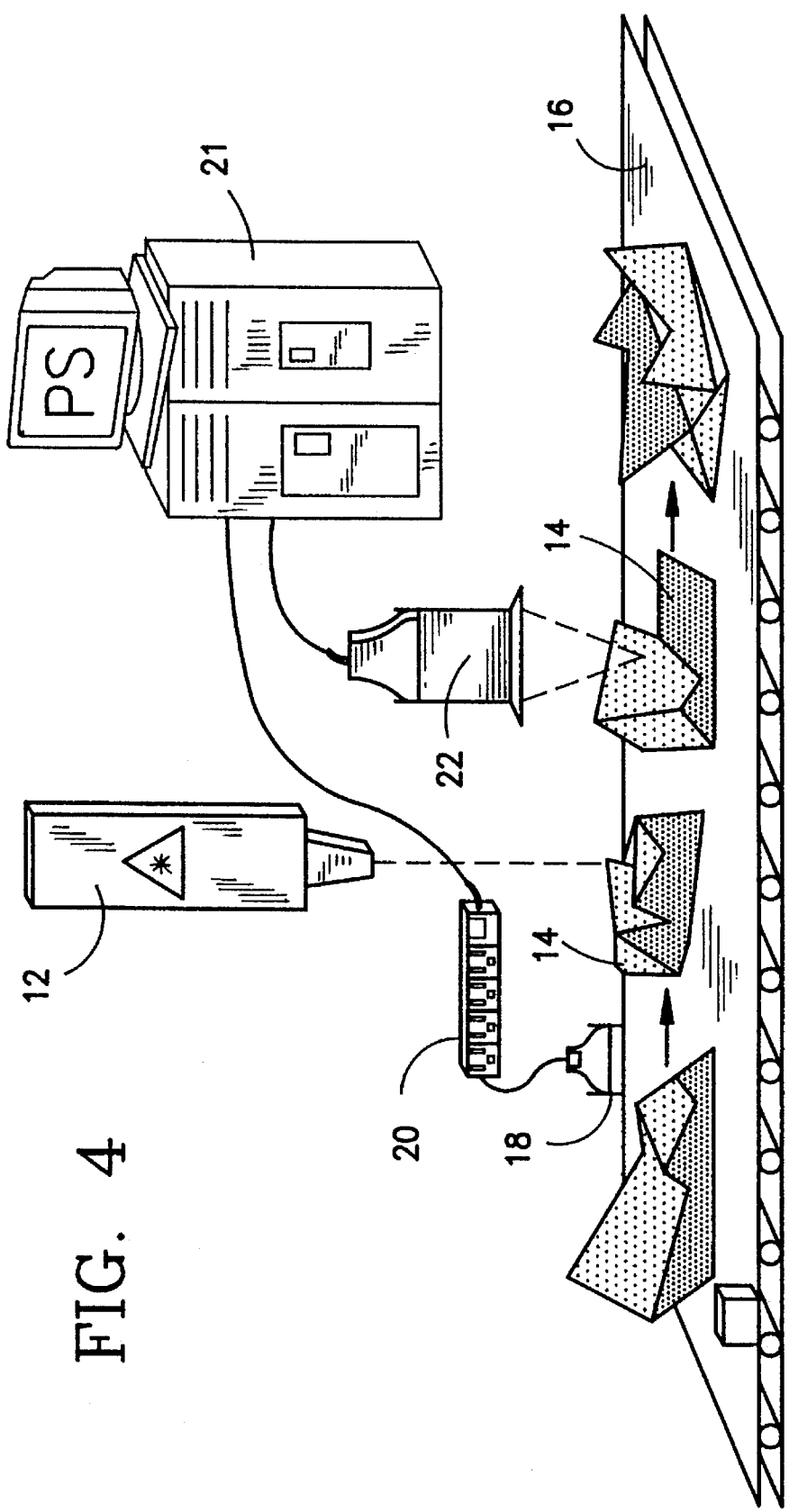
Figure 5:
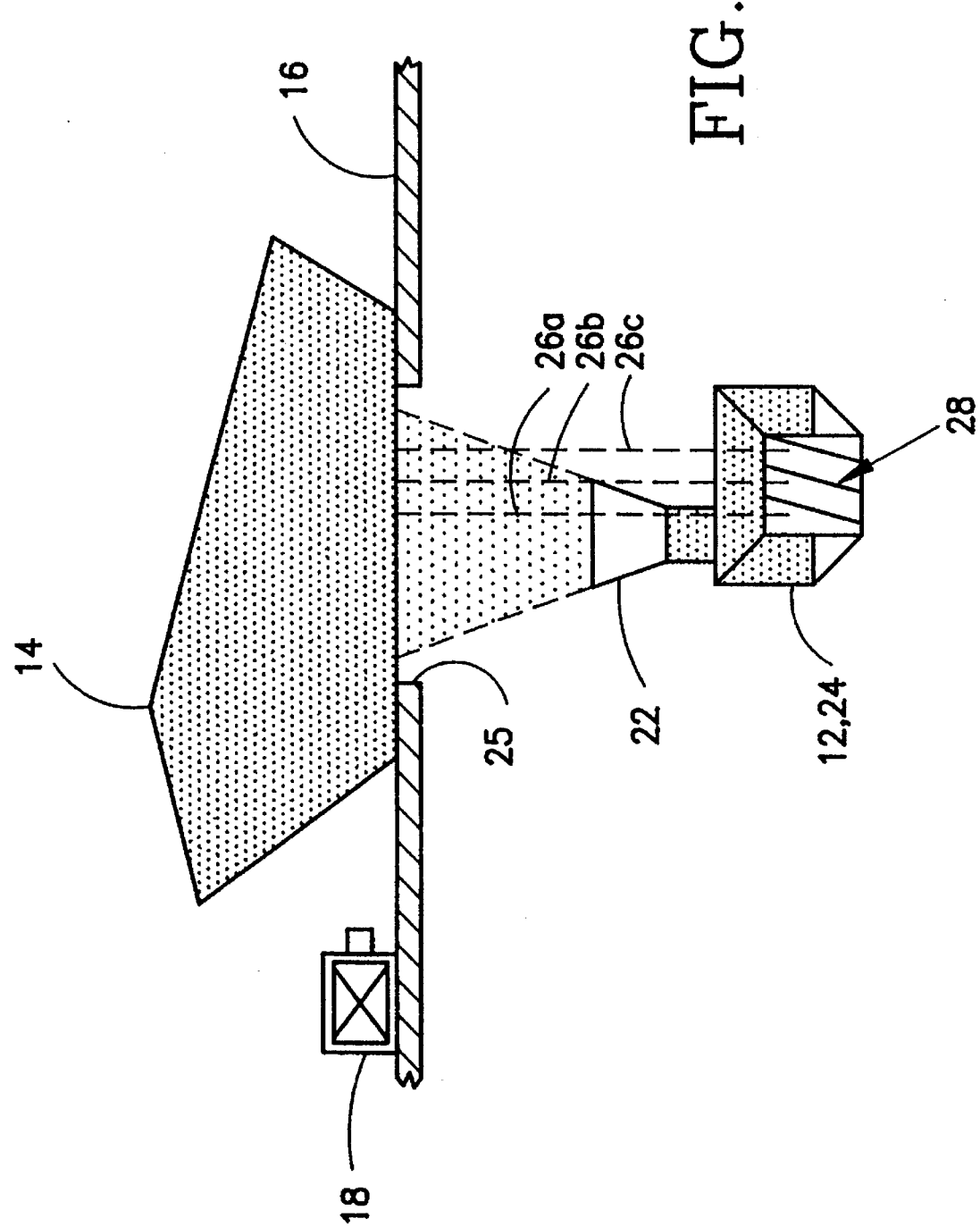
Figure 6:
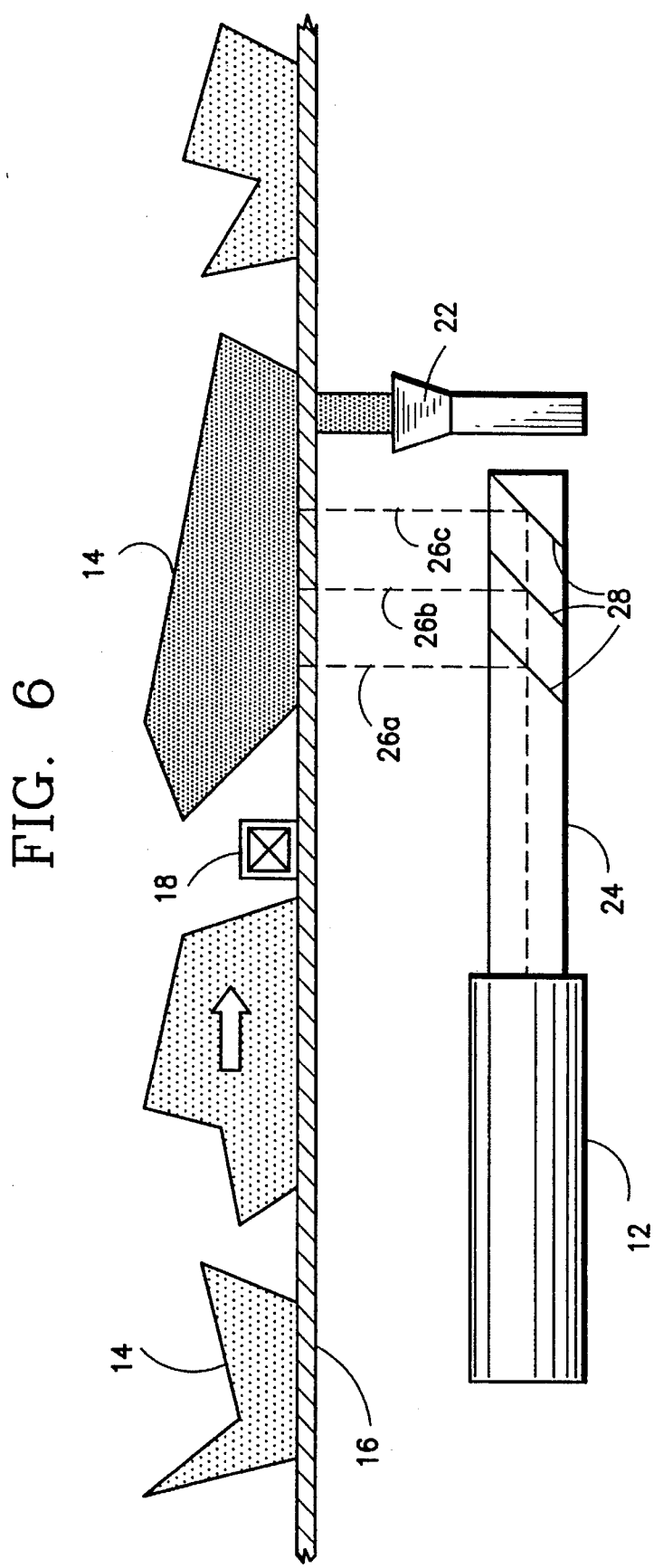
Figure 7:
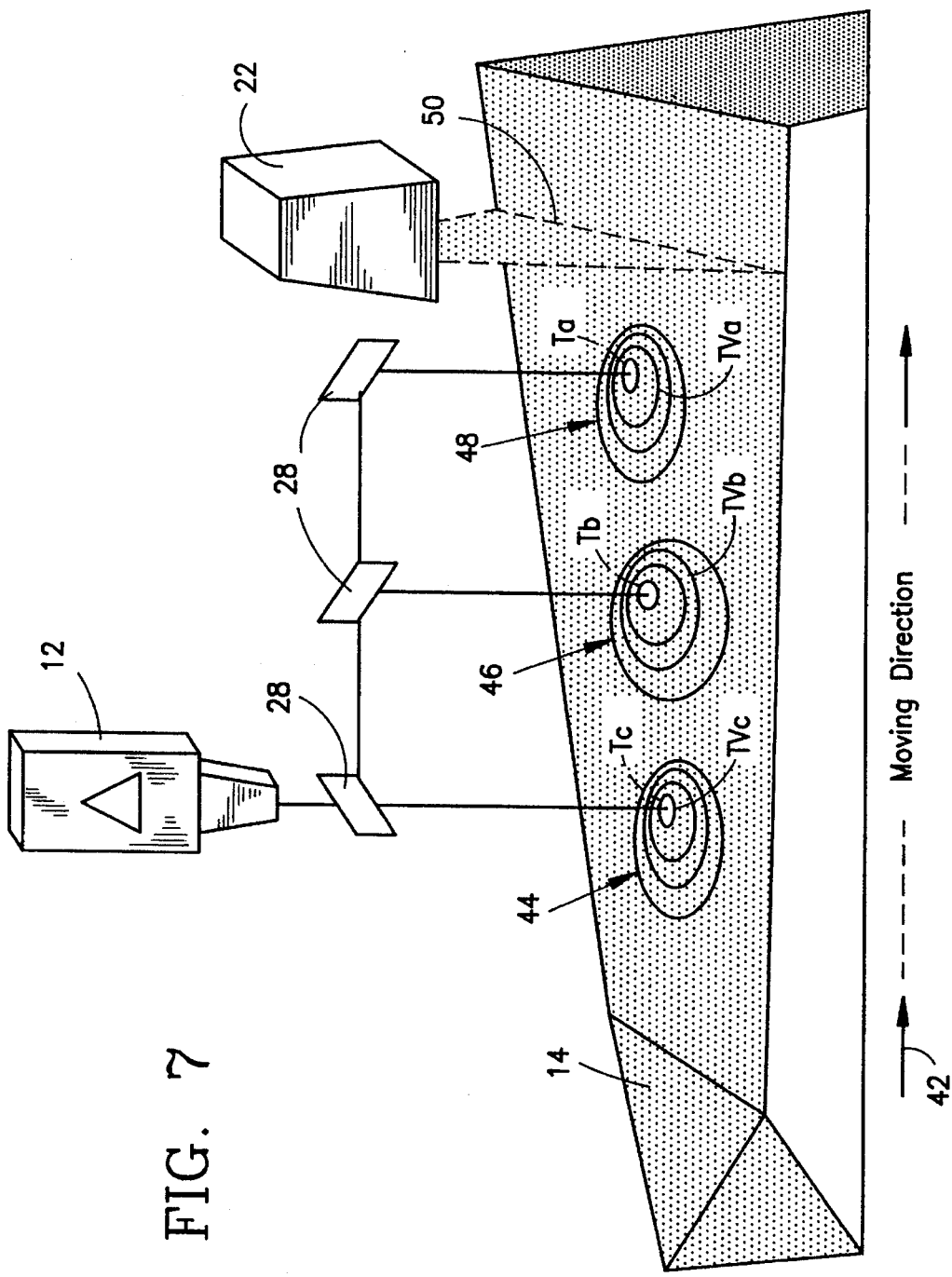
Figure 8:
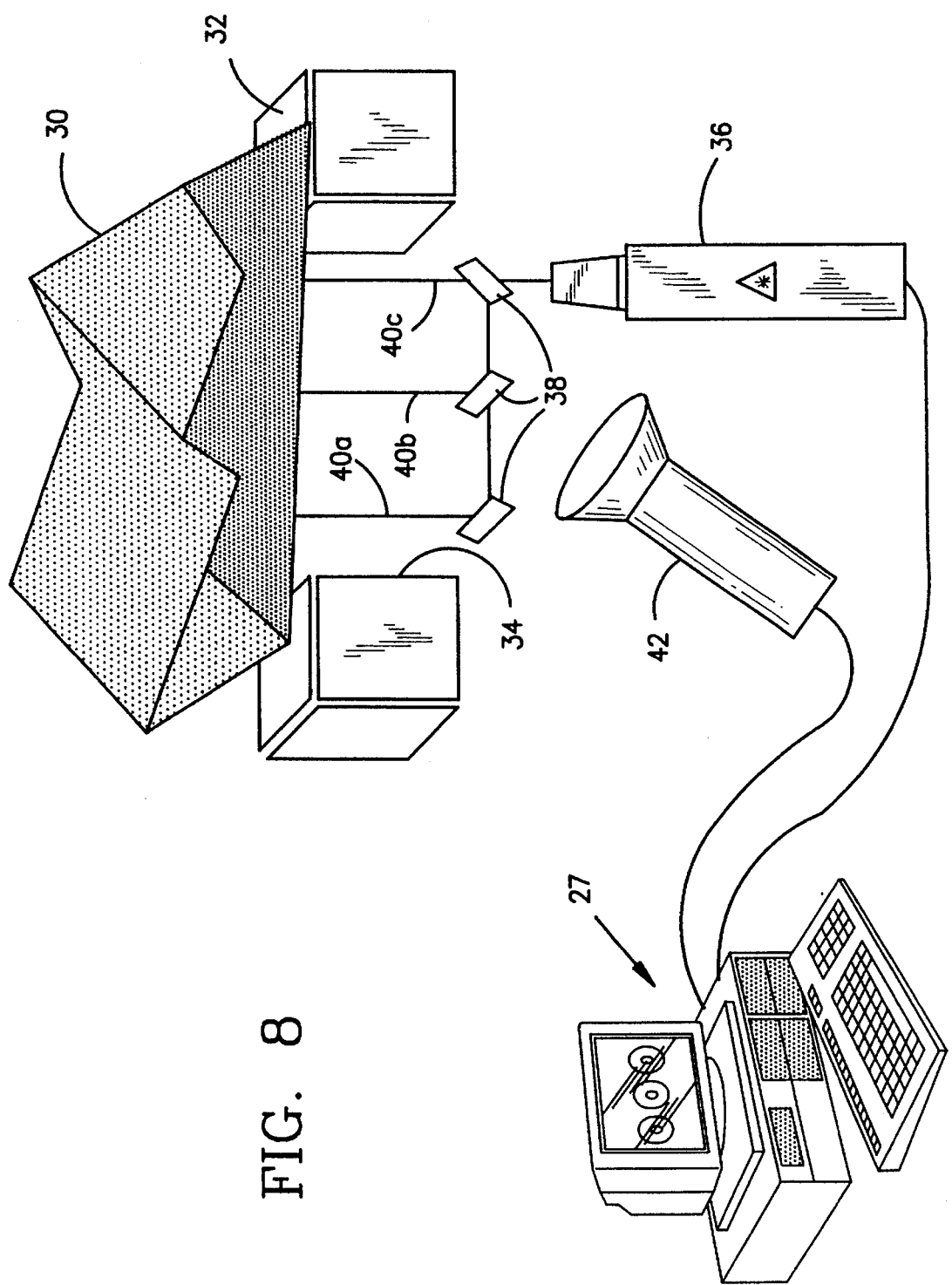
Figure 10:
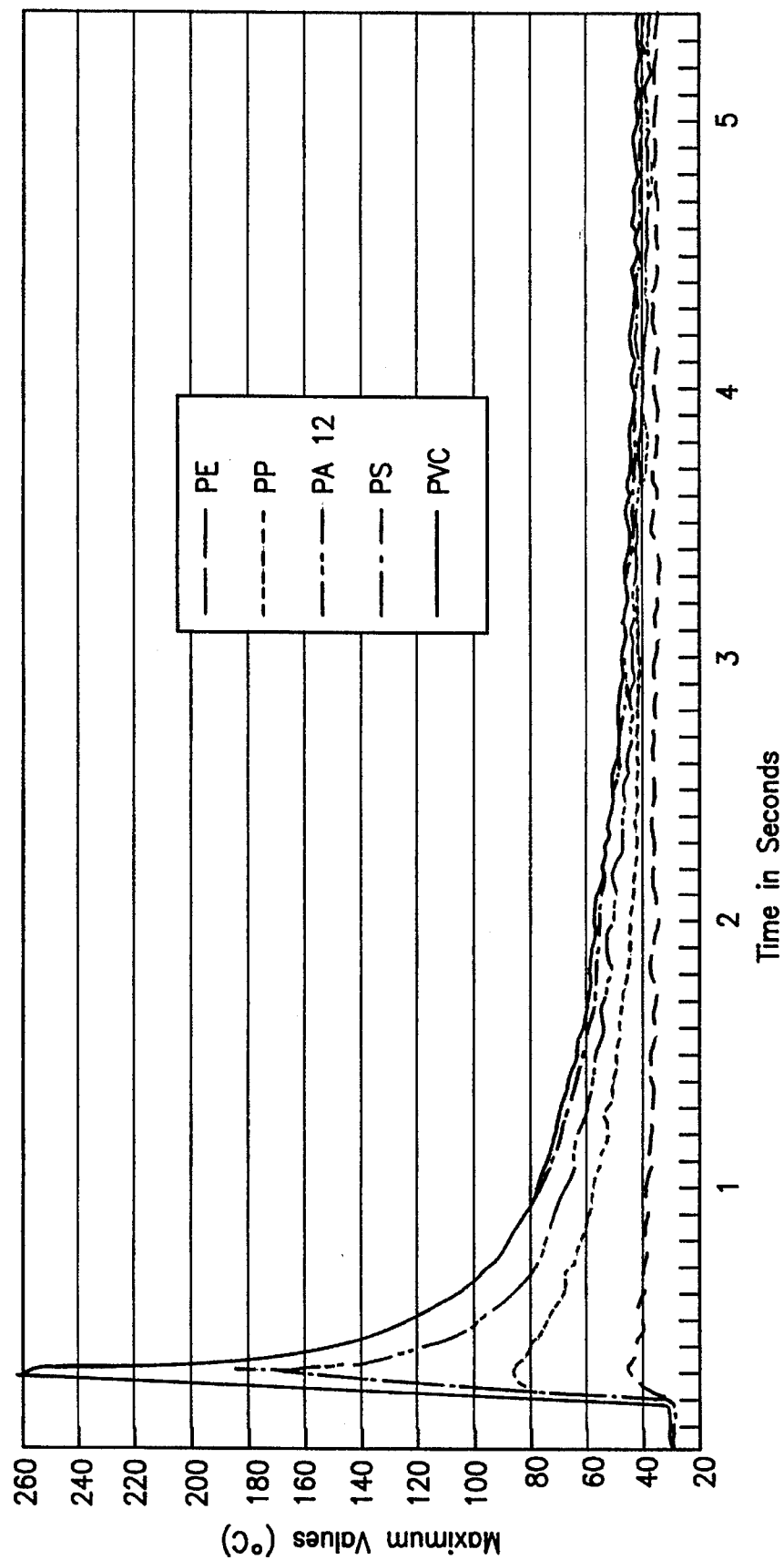
Figure 11:
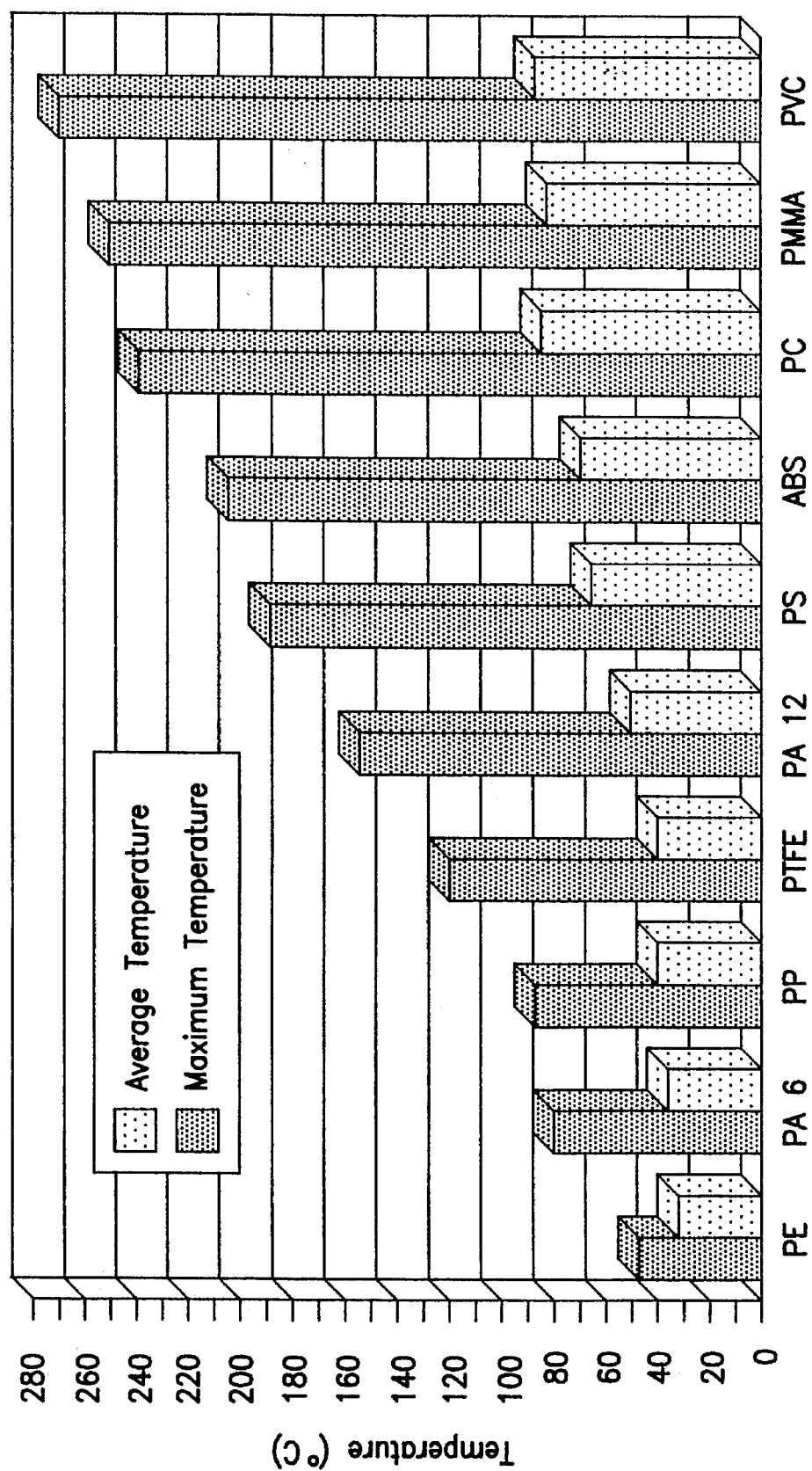
Figure 12:
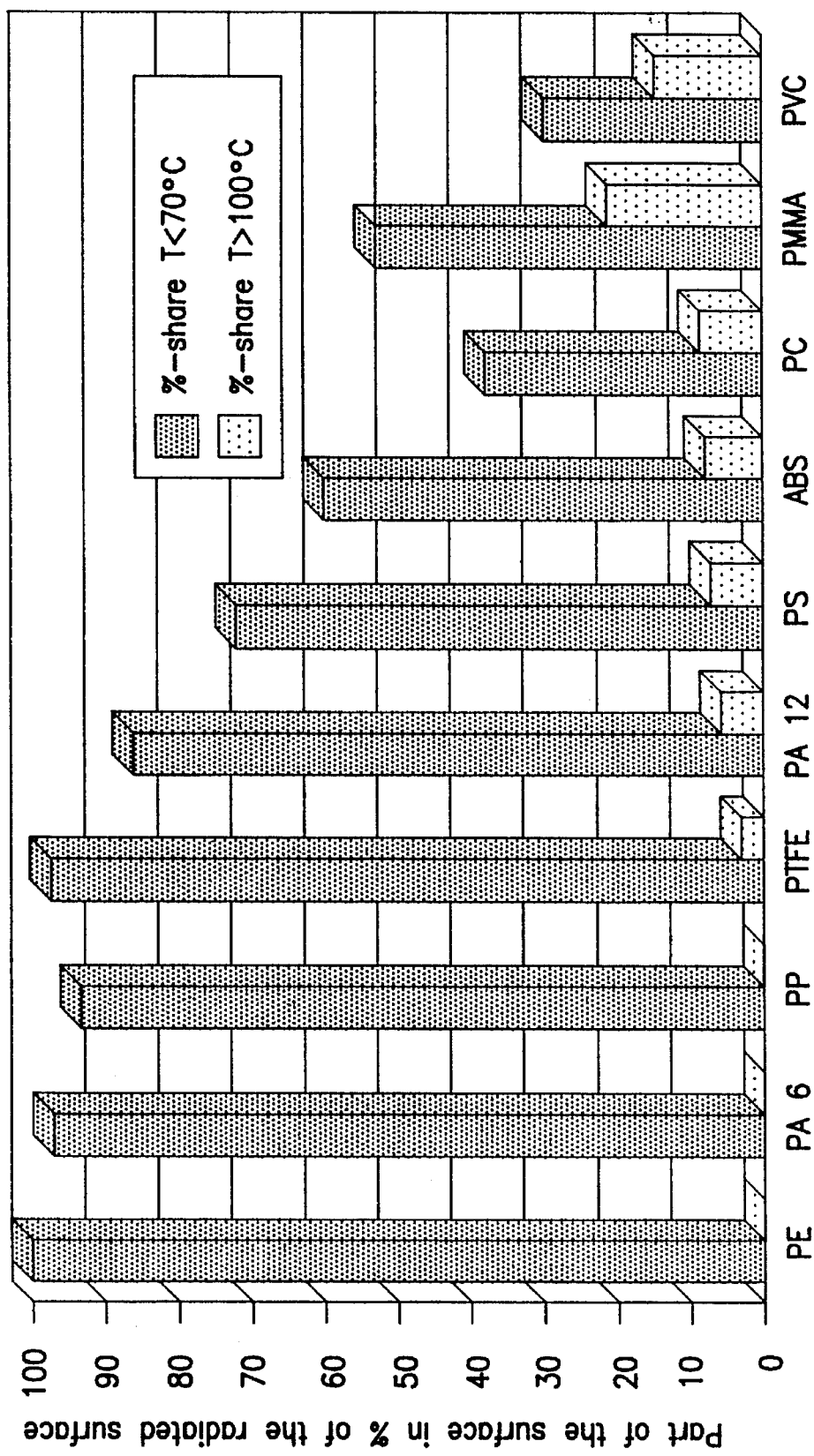
Figure 13:
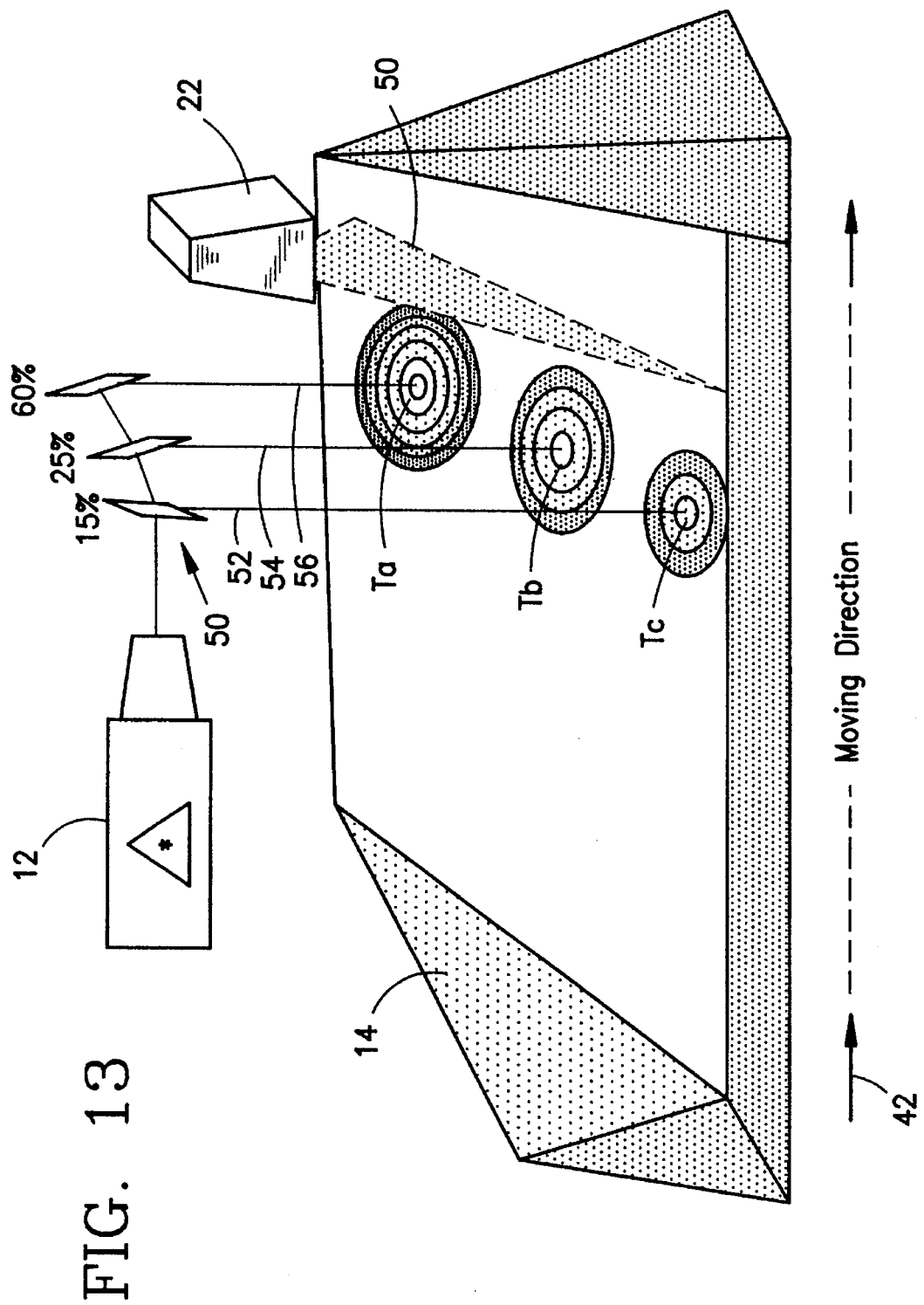

FIG. 1 The principle of an installation for laser-aided material identification;

FIG. 2 A graph of the transmission of different materials, in accordance with the material thickness;

FIG. 3 A graph of the temperature in accordance with the material depth;

FIG. 4 The principle of an installation installation for the laser-aided identification of moving samples;

FIG. 5 The front view of a preferred design of the installation according to FIG. 4;

FIG. 6 The side view of this installation according to FIG. 5;

FIG. 7 An installation for measuring the cooling period of moving materials;

FIG. 8 The principle of an installation for laser-aided identification of stationary materials;

FIG. 9 A list with certain properties of different plastics;

FIG. 10 A graph of temperature-time behaviour of five different plastics;

FIGS. 11 and 12 A graph of the average and maximum temperatures as well as the temperature distribution of the surfaces of different plastics exposed to laser light;

FIG. 13 A installation for the irradiation of several laser impulses of different energy; and FIG. 14 A installation for the use of a laser in the continous wave mode and different wave energies.

In as much as possible, equal parts in the figures have been given the same reference signs.

FIG. 1 shows, schematically, an installation for laser-aided material indentification. A spot 4 on a material 6 which is to be identified is punctually and shortly exposed to laser energy with the aid of a $CO_2$ laser. Laser radiation less than 300 W, and a pulse frequency less than 20 ms can be applied. The thermal impulse response of the material to be identified is immediately recorded after energy injection by means of a thermocamera. For the analysis of the moving samples, an infrared-linescanner is mainly used. Different materials can be examined with respect to their thermal and optical material properties, such as absorption rate, thermal conductivity, thermal capacity and emission rate. In dependancy on these material properties, there are material specific differences in the thermal impulse response of the radiated materials with respect to cooling rates, heat distribution and maximum temperatures. Especially as far as plastics are concerned, the absorption behaviour of the different sorts of plastics differs enormously (FIGS. 2 and 3), which results in a temperature distribution with different maximum temperatures which are especially good to evaluate.

FIGS. 4 to 7 show an installation for laser-aided material identification of moving samples. A $CO_2$ laser with an output of 100 W, for instance, heats materials 14, which are transported through a test section by a conveyer belt 16.

The entrance of the materials into the test section is recorded by a sensor 18, e.g. a lightbarrier, whose output signal is transmitted to a controlling device 21 for triggering the laser pulse. This device controls the laser 12 which irradiates the material passing the sensor controlled, in dependancy on the sensor signal, by means of an electronic data-processor 20. The thermal impulse response is recorded by means of an infrared-linescanner 22, and evaluated by an electronic data-processor 21.

As shown in FIGS. 5 and 6, the laser 12 with its optic 24 is preferentially installed below the moving samples to irradiate the material surface with energy from below. Therefore the conveyer belt 16 has an analytic window 25 through which the energy radiation and the recording of the thermal impulse response is realized. This has the advantage that different distances between sample and analytic system which are caused by different sample sizes are minimized. A second advantage is the minimization of the variation of the surface angle to the analytic system.

Furthermore, the material surface can be simultanously exposed to several laser pulses 26a, 26b, 26c using a beam splitter 28 as shown schematically in FIGS. 5,6 and 7. Here, multiple measuring and identification surely (even as far as stationary samples are concerned) is possible. Furthermore, it offers the possibility to measure cooling rates of moving samples if simultaneous exposure to several laser pulses along the motion axis is realized.

FIG. 7 shows an arrangement for the recording of the cooling period of moving samples 14 in which e.g. as shown three surface regions 44, 46 and 48, arranged one after the other in moving direction, are radiated simultaneously, punctually and quickly by means of the laser 12 and the beam splitter 28, and which afterwards pass, one after the other, the recording section 50 of the infrared linescanner 22. At the same time, the infrared linescanner 22 can measure the maximum temperatures Ta, Tb and Tc, as well as the temperature distributions which are suggested by the isothermals TVa, TVb and TVc.

FIG. 13 shows the arrangement with a beam splitter 50 which provides the possibility to expose the sample surface (e.g. perpendicular to the moving axis) to several laser pulses 52, 54, 56 with different output energies at the same time.

The simultaneous measurement of the different resulting thermal impulse responses offers the advantage of improving the measurable differences between the different materials to be identified (especially as far as plastics are concerned, for possible similar existing thermal impulse responses of various plastics).

1. As far as low absorbing plastics are concerned, such as PE and PP, the application of relatively high laser energies (e.g. at 1–2 mm beam diameter 70 W, 20 ms or 1.4 J) is recommended, to create optimal differences (high temperature differences) of the thermal impulse responses.

2. As far as high absorbing plastics are concerned too high laser energy creates temperatures >250° C. (nearly the melting temperature) which have the disadvantage that, due to the temperatures partial melting or evaporation occurs, which provokes smaller and almost non reproducible temperature distributions (and maximal temperatures), due to the melting and evaporation energy necessary. Consequently, the melting and evaporation heat reduces achievable maximal temperatures to app. 340° C. (without flame creation). To determine high absorbing plastics such as PC, PMMA or PVC, consequently lower laser energy (app. 0.8 J) is advantageous.

Therefore, if several laser pulses of different energy are applied it is possible to reinforce the consequences for the material specific absorption coefficient, and thus to analyse, in a measurement process, more different plastics, and additionally increase identification surely.

As far as the moving material identification is concerned a laser 60 in continous wave operation (pulsed or non-pulsed) with a beam splitter 50 which simultanously emits several laser beams of different energy (see arrangement FIG. 13) can be advantageous, see FIG. 14. A special advantage is that triggering is not necessary, because the moving samples are measured by the laser in any case. Another advantage is an increase in the number of evaluable temperature profiles, because, on the whole radiated material length, evaluable IR-heat radiation observed. Considerable disadvantages of this arrangement are the impossibility to detect the cooling behaviour by means of a line scanner, and the necessity of a higher laser energy absorption and the related shortening of the middle durability of the laser is used.

To avoid damage of the radiated base, if there is no sample to be analyzed in the laser beam, the installation provides a beam absorber (with high heat conductivity and high thermal stability).

The simultanous application of several lasers of different wavelengths offers the advantage of possible consideration of different absorption coefficients which are dependant on the wavelength, and therefore permit an increase in identification surely.

FIG. 8 shows an arrangement for the laser-aided material identification of stationary materials.

The sample which is to be identified lays on a base 32 which has an analysis window 34. A $CO_2$ laser transmits energy to the sample surface from below through the analysis window 34. The laser beam is separated in to several laser beams 40a, 40b, 40c by a multiple beam splitter 38 like in FIGS. 5 and 6, to transmit the energy with several laser pulses simultaneously, punctually and quickly so that multiple measuring is possible, and thus increased identification surely. The thermal impulse response of the materials is recorded by means of a thermocamera 42. It is also possible to use laser pulses of different energy coefficients, like in the arrangements of FIGS. 13 and 14.

The evaluation of the maximum temperature, temperature distribution and cooling rates from the thermal impulse response of the pyrometric temperature measuring device and the recording of an analysis signal (e.g. a sorting signal) is realized by a data processing supported evaluation device 10 and 21, as shown in FIGS. 1, 4 and 8. Here, a reference library as well as a fuzzy logic or neuronal networks are used to evaluate the material specific properties of the thermal impulse response. Adjustment of the recorded thermal image to correct for differences in the angle between the surface of the material and the laser while irradiating can be accomplished with a laser operating in the cw mode.

FIG. 9 shows a diagram of certain material properties of different plastics, and is not to be explained further.

FIG. 10 shows the relation of temperature and time on the surface of radiated plastics, for PVC, PS, PA 12, PP and PE when they were radiated by a laser with, e.g. 60 W for 1/10s, and heated to 262° C. The temperature curves show very clearly the material specific differences of the examined plastics. The smallest but clearly observable difference exists between PP and PA 12.

FIG. 11 shows the maximum temperatures and average temperatures of the radiated surface section directly after the plastics PE, PA 6, PP, PTFE, PA 12, PS, ABS, PC, PMMA, PVC were exposed to the laser energy. The maxima temperatures were measured after energy exposure on within the radiated sample surface section. The great differences between PE, PP, PS, ABS and PVC are peculiar which are present in rubbish as well as in electronic waste recycling. The smallest but evaluable temperature differences of only 7° C. appear between PP and PA 6. Another but also material-specific remit comes from the evaluation of other infrared recording values such as surface distribution within the radiated sample surface, or the ralation between temperature and time.

FIG. 12 shows, for the above mentioned plastics in FIG. 11, the temperature distribution of the radiated surface section directly after the plastics were exposed to the radiation. If the course of the temperature surface parts of the radiated sample surface is examined in per cent, it is clear that, as expected, an increase of surface parts of high temperature (T>100° C.) and a reduction of the surface parts with T<70° C. can be observed. But nevertheless there are important differences which can contribute to an increase in identification surely, if various evaluation methods are considered. Comparing FIGS. 2 and 3, it is clear that in dependant on the evaluation method used, certain material-specific differences can be emphasized. For instance, PC, PMMA and PVC, which are diffucult to define according to FIG. 2, can be defined much easier according to FIG. 3, as far as the evaluation of the temperature surface parts are concerned.

The above-mentioned measurement methods give the following results:

1. Due to the short exposure period to the laser, only a slight damage on the sample surface of the examined plastic took place, which can be ignored.

2. Different thickness, forms and surfaces of the material did not disturb the identification process.

3. The influence of colors and different additives (softeners) also did not disturb the identification process.

4. For all examined plastics PE, PA 6, PP, PTFE, PA 12, PS, ABS, PC, PMMA and PVC at the time of the maximum heating of the plastic, and thus directly after laser radiation, clear material identification could be achieved, due to the temperature evaluation. Analysis of the material within 1/100s is possible.

5. This process for material identification is not only applicable for plastics, but also for every other material such as glass, metals etc., which can be defined with respect to the above mentioned material properties.

6. It is possible to identify materials within other material groups.

We claim:

1. A method for differentiating material comprising the steps of:
   a) providing at least one laser adapted to irradiate the material to be differentiated;
   b) emitting at least one localized, short-duration laser beam from the at least one laser;
   c) directing the emitted laser beam onto the surface area of the material to be differentiated to irradiate and cause heating sufficient to generate a material-specific thermal impulse response;
   d) recording the resultant thermal image of the heated material, the thermal image including at least one of the maximum temperature directly after exposure to the laser, the heat distribution, and the cooling rate of the material after exposure to the laser;
   e) measuring from the recorded thermal image at least one identifying property of the heated material, the property is one selected from the group including coefficient of absorption, thermal conductivity, thermal capacity and emissivity; and
   f) determining the identity of the heated material from the at least one measured physical property.

2. The method as in claim 1 and wherein:
   a) measuring the coefficient of absorption from the maximum temperature recorded directly after exposure to the laser.

3. The method as in claim 1 and wherein:
   a) measuring the thermal conductivity from the heat distribution recorded after a defined period of cooling.

4. The method as in claim 1 and wherein:
   a) measuring the coefficient of absorption from the heat distribution recorded directly after exposure to the laser.

5. The method as in claim 1 and wherein:
   a) measuring the thermal conductivity from the cooling rate recorded after exposure to the laser.

6. The method as in claim 1 and wherein:
   a) recording the thermal image of the heated material with a pyrometric temperature measurement device selected from one of a thermocamera, an IR-linescanner and a pyrometer.

7. The method as in claim 1 and further including the step of:
   a) providing a trigger signal to selectively actuate the laser for irradiation of moving material.

8. The method as in claim 1 and further including the step of:
   a) pulsing the localized, short-duration laser beam.

9. The method as in claim 1 and further including the step of:
   a) simultaneously irradiating the material with beams having different intensities.

10. The method as in claim 1 and further including the step of:
    a) simultaneously irradiating the material with beams having different wavelengths.

11. The method as in claim 1 and further including the steps of:
    a) moving the material while irradiating with the laser beam, and
    b) directing the laser beam along the axis of motion of the material to evenly expose the material throughout the working area of the laser.

12. The method as in claim 1 and further including the step of:
    a) adjusting the recorded thermal image to correct for differences in the angle between the surface of the material and the laser while irradiating.

13. The method as in claim 12 and wherein:
    a) adjusting the recorded thermal image by providing a laser operable in the cw mode.

14. The method as in claim 1 and wherein:
    a) emitting the short-duration laser beam for a period of about <50 msec.

15. The method as in claim 1 and wherein:
    a) the short-duration laser beam has a diameter of about <2 mm.

16. The method as in claim 1 and wherein:
    a) the short-duration laser beam has an output of about 100 watts.

17. A system for differentiating material by heating the surface thereof, comprising:
    a) at least one means for irradiating the material to be differentiated, said irradiating means adapted to emit at least one localized, short-duration energy beam;
    b) means to direct said emitted energy beam onto the surface area of the material to be differentiated to irradiate and cause heating sufficient to generate a material-specific thermal impulse response;
    c) means for recording the resultant thermal image of the heated material, the thermal image including at least one of the maximum temperature directly after exposure to said irradiating means, the heat distribution, and the cooling rate of the material after exposure to said irradiating means;
    d) means for measuring from the recorded thermal image at least one identifying property of the heated material, the property is one selected from the group including coefficient of absorption, thermal conductivity, thermal capacity and emissivity; and
    e) means for determining the identity of the heated material from the at least one measured physical property.

18. The system of claim 17, wherein:
    a) said recording means is one of a thermocamera, IR-linescanner and a pyrometer.

19. The system of claim 17 and further including:
    a) means for conveying the material during irradiation; and b) means for providing a trigger signal, said trigger signal means operatively associated with said conveying means and said irradiating means to provide selective irradiation of the material as it is conveyed.

20. The system of claim 19 and wherein:

a) said directing means is at least one beam splitter adapted to selectively direct said beam either parallel to or perpendicular to the direction of movement of the material.

21. The system of claim 17 and wherein:

a) said directing means is at least one beam splitter adapted to provide multiple beams having different intensities.

22. The system of claim 17 and wherein:

a) said irradiating means, directing means and recording means are positioned underneath the material.

23. The system of claim 17 and wherein:

a) said irradiation means is a $CO_2$ laser.

24. The system of claim 17 and wherein:

a) said irradiation means comprises multiple lasers, each of which have a different wavelength.

* * * * *